United States Patent [19]
Yernool et al.

[11] Patent Number: 6,150,171
[45] Date of Patent: Nov. 21, 2000

[54] THERMOSTABLE ALPHA-GALACTOSIDASE AND METHODS OF USE

[75] Inventors: Dinesh Yernool, Piscataway; Douglas E. Eveleigh, Rocky Hill, both of N.J.; Michael R. King, Oswego; Bruce Chassy, Champaign, both of Ill.

[73] Assignees: Rutgers, The State University of New Jersey, New Brunswick, N.J.; The Board of Trustees of the University of Illinois, Urbana, Ill.

[21] Appl. No.: 09/138,172

[22] Filed: Aug. 21, 1998

Related U.S. Application Data

[60] Provisional application No. 60/057,047, Aug. 22, 1997.
[51] Int. Cl.$^7$ .............................. C12N 5/04; C12N 15/31; C12N 15/56; C12N 15/82; A01H 5/10
[52] U.S. Cl. .................. 435/468; 435/69.1; 435/320.1; 435/415; 435/419; 536/23.7; 800/284; 800/288; 800/298; 800/312
[58] Field of Search ................................ 435/69.1, 320.1, 435/410, 415, 419, 468; 536/23.7; 800/278, 284, 288, 295, 298, 312

[56] References Cited

U.S. PATENT DOCUMENTS 5,543,576   8/1996   Van Ooijen et al. .................... 800/278

FOREIGN PATENT DOCUMENTS

WO 97/25417   7/1997   WIPO .............................. C12N 9/26

OTHER PUBLICATIONS

McCabe et al, Bio/technology, vol. 6, pp. 923–926, 1988.

Michael R. King, et al. Thermostable α–galactosidase from *Thermotoga neapolitana:* cloning, sequencing and expression. *FEMS Microbiology Letters.* 1998 163: 37–42.

Guy D. Duffaud, et al. Purification and Characterization of Extremely Thermostable β–Mannanase, β–Mannosidase, and α–Galactosidase from the Hyperthermophilic *Eubacterium Thermotoga neapolitana* 5068. *Applied and Environmental Microbiology.* 1997 64: 169–177.

Richard Schuler, et al. Kinetic Properties of α–D–galactosidase from *Lactobacillus fermenti*. *Enzyme Microbiology Technology.* 1985 7: 207–211.

K. Schmid, et al. Raffinose Metabolism in *Escherichia coli* K12 Purification and Properties of a New α–Galactosidase Specified by a Transmissible Plasmid. *The Journal of Biochemistry.* 1976 67: 95–104.

Richard I. Somiari, et al. Properties of an extracellular glycosidase of *Aspergillus niger* suitable for removal of oligosaccccharides from cowpea meal. *Enzyme and Microbiology Technology.* 1995 17: 311–316.

Roger A. Korus, et al. The use of α–Galactosidase and invertase in Hollow Fiber Reactors. *Biotechnology and Bioengineering.* 1977 19: 1–8.

Darunee Thananunkul, et al. Degradation of Raffinose and Stachyose in Soybean Milk by A–Galactosidase from *Mortierella vinacea*. Entrapment of α–galactosidase within polyacrylamide gel. *The Journal of Food Science.* 1976 41: 173–174.

G. Talbot, et al. Purification and Characterization of thermostable β–Mannanase and α–Galactosidase from *Bacillus stearothermophilus*. *Applied and Environmental Microbiology.* 1990: 3305–3510.

Masaru Mitsutomi, et al. Isolation and identification of oligosaccharides Produced from Raffinose by Transgalactosylation Reaction of Thermostable α–Galactosidase from *Pycnoporus cinnabarinus*. *Agriculture Biological Chemistry.* 1998 52: 2305–2311.

Marisa S. Garro, et al. Purification of α–galactosidase from *Lactobacillus fermentum*. *Journal of Biotechnology.* 1996 45: 103–109.

Hiroyuki Hashimoto, et al. Purification and Some Properties of α–Galactosidase from *Pseudomonas fluorescens* H–601. *Agriculture Biological Chemistry.* 1991 55: 2831–2838.

C. Leuschner, et al. Heat–stable enzymes from extremely thermophilic and hyperthermophilic microorganisms. *World Journal of Microbiology and Biotechnology.* 1995 II: 95–114.

Satoshi Ishii, et al. The functional role of glutamine–280 and threonine–282 in human α–galactosidase. *Biochimica et Biophysica Acta.* 1995 1270: 163–167.

Alex Zhu, et al. Identification of tyrosine 108 in coffee bean α–galactosidase as an essential residue for the enzyme activity. *Biochimica et Biophysica Acta.* 1995 1247: 260–264.

Santiago Rios, Purification and Molecular Properties of an α–galactosidase synthesized and secreted by *Aspergillus nidulans*. *FEMS Microbiology Letters.* 1993 112: 35–42.

Susanne Zeilinger, et al. Conditions of Formation, Purification, and Characterization of an α–Galactosidase of *Trichoderma reesei* RUT C30. *Applied and Environmental Microbiology.* 1993 59: 1347–1353.

Carol M. McCutchen, et al. Characterization of Extremely Thermostable enzymatic Breakers (α–1.6–Galactosidase and β–1,4–Mannanase) from the Hyperthermophilic Bacterium *Thermotoga Neapolitana* 5068 for Hydrolysis of Guar Gum. *Biotechnology and Bioengineering.* 1996 52: 332–339.

Ramachandran Murali, et al. Crystallization and Preliminary X–ray Analysis of Human α–Galactosidase A Complex. *The Journal Molecular Biology.* 1994 239: 578–580.

(List continued on next page.)

*Primary Examiner*—Lynette R. F. Smith
*Assistant Examiner*—Ashwin D. Mehta
*Attorney, Agent, or Firm*—Janet E. Reed; Saul Ewing Remick & Saul, LLP

[57] ABSTRACT

An isolated nucleic acid from the bacterium *Thermotoga neapolitana*, encoding a thermostable α-galactosidase is provided. The Thermotoga gene is cloned into a high expression vector to provide large quantities of a purified thermostable α-galactosidase. The thermostable enzyme is used in high-temperature processing of soy products to remove α-galactosides.

12 Claims, 6 Drawing Sheets

OTHER PUBLICATIONS

Jill E. Porter, et al. Ion Exchange and Affinity chromatography in the Scaleup of the Purification of α–Galactosidase from Soybean Seeds. *Biotechnology and Bioengineering.* 1991 37: 356–363.

John H. Reynolds, An Immobilized α–Galactosidase Continuous Flow Reactor *Biotechnology and Bioengineering.* 1974 16: 135–147.

Yoshinori Koyama, et al. Cloning of α–Galactosidase Genes from an Extreme Thermophile, Thermus Strain T2, and Their Expression in *Thermus thermophilus* HB27. *Applied and Environmental Microbiology.* 1990 56: 2251–2254.

Charalampos Aslanidis, et al. Nucleotide Sequences and Operon Structure of Plasmid–Borne Genes Mediating Uptake and Utilization of Raffinose in *Escherichia Coli*A. *The Journal of Bacteriology.* 1989 171: 6753–6763.

Kenji Sakai, et al. Hydrolysis of α–Galactosyl Oligosaccharides in Soymilk by α–Galactosidase of Bifidobacterium breve 203. *Agriculture Biology Chemistry.* 1987 51: 315–322.

Marisa S. Garro, et al. Characterization of Alpha–Galactosidase from *Lactobacillus fermentum*. *The Journal of Bacteriology.* 1993 75: 485–488.

Frank Gherardini, et al. Purification and Characterization of Two α–Galactosidases Associated with Catabolism of Guar and Other α–Galactosides by *Bacteroides ovatus*. *The Journal of Bacteriology.* 1985 161: 500–506.

V.H. Mulimani, et al. Enzymic Hydrolysis of Raffinose and Stachyose in Soymilk by Alpha–Galactosidase from Gibberella Fujikuroi. *Biochemistry and Molecular Biology International.* 1995 36: 897–905.

M.C.M. Hensing, et al. Effects of Cultivation Conditions on the Production of Heterologous α–Galactosidase by *Kluyveromyces lactis. Applied Microbiology Biotechnology.* 1995 43: 58–64.

K. L. Smiley, et al. Alpha–Galactosidase Production and Use in a Hollow–Fiber Reactor. *Applied and Environmental Microbiology.* 1976 31: 615–617.

FIG. 1-1

```
801                                                                            900
    GGATGTGTTCAACTCCTATCCGGACTGGGTCGTGAAGGAAAACGAATCCAAGATGGCTACCAGGAACTGAAGATCTACGCTCTTGACCTT
     D  V  F  N  S  Y  P  D  W  V  V  K  E  N  G  M  P  K  M  A  Y  R  N  W  N  R  K  I  Y  A  L  D  L
901                                                                            1000
    TCAAACAAGAGTCCTGGACTGGCTCTTCAGCCTCTTCAAGATACTTCAAGATGGCTACAGATACTTCAAGATCGACTTCTTCTTTGCAGGAGCGA
     S  N  K  E  V  L  D  W  L  F  D  L  F  S  S  L  K  K  M  G  Y  R  Y  F  K  I  D  F  L  F  A  G  A
1001                                                                           1100
    TTCCGGGTGAGAGGAAGAAAAACATCACACCGGTTCAGGGGTTCAGAAAGGGATGAAGTGATCAGAAAGGCGGTTGAGACTGTCATACTGGATG
     I  P  G  E  R  K  E  N  I  T  P  V  Q  A  F  R  K  G  M  E  V  I  R  K  A  V  G  D  L  F  I  L  G  C
1101                                                                           1200
    TGGCTCTCCCTCTCTCCTGGGGTGGGCTAGTTGAGGCATGAGGGATAGGGCCGGGACAACCACCACACCCTCTGGGTGATCAAATAGAAGACAAGGACGA
     G  S  P  L  L  P  A  V  G  Y  V  D  G  M  R  I  G  P  D  T  T  P  F  W  G  D  Q  I  E  D  N  G  A
1201                                                                           1300
    CCGCTGCAAGATGGCTCTCGAGAGAAATGGCATCACAGTTACTTCATGCACGACAGACTCCTGCTGATCCTGAGAGAGGAA
     P  A  A  R  W  A  L  R  N  A  I  T  R  Y  F  M  H  D  R  L  W  L  N  D  P  D  C  L  I  R  E  E
1301                                                                           1400
    AAACAACTGACCCAAAGAGAGAGGAGCTCTACTCTGTGGATCTCGACACATAGAAAGTGACACTGACTGTGAAGA
     K  T  E  L  T  P  K  E  R  E  L  Y  S  Y  T  C  G  I  L  D  N  M  I  E  S  D  D  L  S  V  K  E
1401                                                                           1500
    GCACGGAAGGAGGTTCTCAGAGACACTCGACATCTCTGGGGCGAAAGCCCGGTGTTCTGAACATCATGACAGAGGATCTGAAGTACGAGATCGTCTCG
     H  G  R  K  V  L  R  E  T  L  D  L  L  G  G  K  P  R  V  L  N  I  M  T  E  D  L  K  Y  E  I  V  S
1501                                                                           1600
    TCTGGCAGATCTCTGAAACACCAGGCTGTTGTGATCTCAAAAACAGAGTACATCTGAAAAGAGGAAAGTCCTCTGAGAAGAAGGTTG
     S  G  T  I  S  G  N  T  R  L  V  V  D  L  K  N  R  E  Y  H  L  E  K  E  G  K  S  S  L  R  K  K  V
1601
    TCAAAGAGAGACGGAAGAAACTTCTACTTCTACGAAGAGGGTGAGAGAGAATGA
     V  K  R  E  D  G  R  N  F  Y  F  Y  E  E  G  E  R  E Stp
```

FIG. 1-2

Retention times: 7.63 = buffer
7.91 = stachyose
8.41 = raffinose
9.2 = sucrose
12.44-12.61 = galactose ary sources have been used to remove flatulence factors in soy: these include Bifidiobacterium sp. (Sakai, et al., 1987); *Aspergillus awamori* (Simley, et al., 1976); A niger (Somiari and Balogh, 1995) and *L. fermentum* (Garro et al., 1996). Mulamani and Ramalingam (1995) obtained complete hydrolysis of stachyose and 60% hydrolysis of raffinose in 2.5 hrs. using a *Gibberrella fujikuroi* α-galactosidase in soy milk, while Schuler et al., (1985) completely hydrolyzed α-galactosides in commercial soy milk samples with an α-galactosidase from *L. fermenti*. In addition, immobilized enzyme systems have been developed using α-galactosidase from *Moritierella vinacea* (Thananunkal, et al., 1976) and *B. stearothermophilus* (Korous and Olson, 1977; Reynolds, 1974). None of these enzymatic processes have gained commercial acceptance as they suffer from the lack of enzyme stability, while their low operating temperatures and prolonged periods of incubation can result in the growth of microbial contaminants. In contrast, enzymatic processes could be commercially competitive by using highly thermostable enzymes with sustained activity above 80° C. Moreover, inasmuch as even thermostable enzymes are costly to purify from their natural sources, an even greater cost benefit is obtained by isolating and purifying the genes encoding these enzymes, for the purpose of producing the enzymes by recombinant means.

SEQUENCE LISTING

<160> NUMBER OF SEQ ID NOS: 4

<210> SEQ ID NO 1
<211> LENGTH: 1783
<212> TYPE: DNA
<213> ORGANISM: Thermotoga neapolitana

<400> SEQUENCE: 1

```
agagcacctc gtatccacca gtctgaacac gggaaaaacc atctatgtga ggtgatctgt      60
gtggagatct tcaaaagacc gttcagagaa gggagcttcg ttctgaaaga gaaggactac     120
accgttgagt tcgaggtgga gaagatccat cttggatgga agatttcagg gagagtgaag     180
ggaaatcccg gaaggcttga gatctttcgg acaaacgcac cgaagaaact cctcgtgaac     240
aactggcagt cctggggacc ctgcagggtg gtggatcttc catccttcac cccacccgag     300
atagatccaa actggcagta cacggcctct gtggtaccgg atgtgatcaa aaaccgtctt     360
cagagtgact acttcgtggc agaggaaggg agagtatacg gttttttgag ttcgaagatc     420
gcacatcctt tctttgcggc agagaatgga gaacttgttg cgtatcttga gtacttcgat     480
gtgaagttcg atgacttcgt tccgatagaa ccttttgtcg ttcttgaaga tccaaacacc     540
```

```
tctctccttc tggaaaagta cgctgaactc gtcgggaagg aaaacagcgc gaggattcca      600
gaacgtacac cggttggatg gtgcagctgg taccactatt tcctcgatct cacctgggag      660
gagactttga agaatctgga acttgcagga gagtttccct tcgaggtctt tcagatagac      720
gacgcgtatg aaaaagacat cggagactgg ctcgtcacga agaaagactt cccatctgtg      780
gacgagatgg caaggacgat acaggagaaa ggctttgttc ctggtatatg gaccgcaccg      840
ttcagtgttt cagaaacatc ggatgtgttc aactcctatc cggactgggt cgtgaaggaa      900
aacggaatgc caaagatggc gtacaggaac tggaacagaa gatctacgc tcttgacctt      960 tcaaacaaag aagtcctgga ctggctcttc gacctcttca gctctctcaa gaagatgggc     1020
tacagatact tcaagatcga ctttctcttt gcaggagcga ttccgggtga gaggaaagaa     1080
aacatcacac ccgttcaggc gttcagaaag gggatggagg tgatcagaaa ggcggttgga     1140
gacttgttca tactcggatg tggctctccc cttcttcctg cggtgggcta cgttgacggc     1200
atgaggatag ggccggacac cacacccttc tggggtgatc aaatagaaga caacggagca     1260
cccgctgcaa gatgggctct gagaaatgcc atcacacgtt acttcatgca cgacagactc     1320
tggctgaacg atccggactg cctcatcctg agagaggaaa aaacagaact gaccccaaaa     1380
gagagagagc tctactcgta cacctgtggg atcctcgaca acatgatcat agaaagtgac     1440
gacctgtcac ttgtgaaaga gcacggaagg aaggttctga gagagacact cgatcttctc     1500
gggggaaagc cccgtgttct gaacatcatg acagaggatc tgaagtacga gatcgtctcg     1560
tctggcacga tctctggaaa caccaggctc gttgtcgatc tcaaaaacag agagtaccat     1620
ctggaaaaag agggaaagtc ctctctgaga agaaggttg tcaaaagaga agacggaaga     1680
aacttctact tctacgaaga gggtgagaga gaatgagaga gaatgatgga actcaggtac     1740
aacccgctca cagacgaatg ggtgatcatc tccgctgcaa cac                       1783
```

<210> SEQ ID NO 2
<211> LENGTH: 551
<212> TYPE: PRT
<213> ORGANISM: Thermotoga neapolitana

<400> SEQUENCE: 2

```
Val Glu Ile Phe Lys Arg Pro Phe Arg Glu Gly Ser Phe Val Leu Lys
1               5                   10                  15

Glu Lys Asp Tyr Thr Val Glu Phe Glu Val Glu Lys Ile His Leu Gly
                20                  25                  30

Trp Lys Ile Ser Gly Arg Val Lys Gly Asn Pro Gly Arg Leu Glu Ile
            35                  40                  45

Phe Arg Thr Asn Ala Pro Lys Lys Leu Leu Val Asn Asn Trp Gln Ser
        50                  55                  60

Trp Gly Pro Cys Arg Val Val Asp Leu Pro Ser Phe Thr Pro Pro Glu
65                  70                  75                  80

Ile Asp Pro Asn Trp Gln Tyr Thr Ala Ser Val Val Pro Asp Val Ile
                85                  90                  95

Lys Asn Arg Leu Gln Ser Asp Tyr Phe Val Ala Glu Gly Arg Val
                100                 105                 110

Tyr Gly Phe Leu Ser Ser Lys Ile Ala His Pro Phe Ala Ala Glu
            115                 120                 125

Asn Gly Glu Leu Val Ala Tyr Leu Glu Tyr Phe Asp Val Lys Phe Asp
        130                 135                 140

Asp Phe Val Pro Ile Glu Pro Phe Val Val Leu Glu Asp Pro Asn Thr
```

```
                145                 150                 155                 160
        Ser Leu Leu Leu Glu Lys Tyr Ala Glu Leu Val Gly Lys Glu Asn Ser
                        165                 170                 175
        Ala Arg Ile Pro Glu Arg Thr Pro Val Gly Trp Cys Ser Trp Tyr His
                        180                 185                 190
        Tyr Phe Leu Asp Leu Thr Trp Glu Thr Leu Lys Asn Leu Glu Leu
                        195                 200                 205
        Ala Gly Glu Phe Pro Phe Glu Val Phe Gln Ile Asp Asp Ala Tyr Glu
                        210                 215                 220
        Lys Asp Ile Gly Asp Trp Leu Val Thr Lys Lys Asp Phe Pro Ser Val
        225                 230                 235                 240
        Asp Glu Met Ala Arg Thr Ile Gln Glu Lys Gly Phe Val Pro Gly Ile
                        245                 250                 255
        Trp Thr Ala Pro Phe Ser Val Ser Glu Thr Ser Asp Val Phe Asn Ser
                        260                 265                 270
        Tyr Pro Asp Trp Val Val Lys Glu Asn Gly Met Pro Lys Met Ala Tyr
                        275                 280                 285
        Arg Asn Trp Asn Arg Lys Ile Tyr Ala Leu Asp Leu Ser Asn Lys Glu
                        290                 295                 300
        Val Leu Asp Trp Leu Phe Asp Leu Phe Ser Ser Leu Lys Lys Met Gly
        305                 310                 315                 320
        Tyr Arg Tyr Phe Lys Ile Asp Phe Leu Phe Ala Gly Ala Ile Pro Gly
                        325                 330                 335
        Glu Arg Lys Glu Asn Ile Thr Pro Val Gln Ala Phe Arg Lys Gly Met
                        340                 345                 350
        Glu Val Ile Arg Lys Ala Val Gly Asp Leu Phe Ile Leu Gly Cys Gly
                        355                 360                 365
        Ser Pro Leu Leu Pro Ala Val Gly Tyr Val Asp Gly Met Arg Ile Gly
        370                 375                 380
        Pro Asp Thr Thr Pro Phe Trp Gly Asp Gln Ile Glu Asp Asn Gly Ala
        385                 390                 395                 400
        Pro Ala Ala Arg Trp Ala Leu Arg Asn Ala Ile Thr Arg Tyr Phe Met
                        405                 410                 415
        His Asp Arg Leu Trp Leu Asn Asp Pro Asp Cys Leu Ile Leu Arg Glu
                        420                 425                 430
        Glu Lys Thr Glu Leu Thr Pro Lys Glu Arg Glu Leu Tyr Ser Tyr Thr
                        435                 440                 445
        Cys Gly Ile Leu Asp Asn Met Ile Ile Glu Ser Asp Asp Leu Ser Leu
                        450                 455                 460
        Val Lys Glu His Gly Arg Lys Val Leu Arg Glu Thr Leu Asp Leu Leu
        465                 470                 475                 480
        Gly Gly Lys Pro Arg Val Leu Asn Ile Met Thr Glu Asp Leu Lys Tyr
                        485                 490                 495
        Glu Ile Val Ser Ser Gly Thr Ile Ser Gly Asn Thr Arg Leu Val Val
                        500                 505                 510
        Asp Leu Lys Asn Arg Glu Tyr His Leu Glu Lys Glu Gly Lys Ser Ser
                        515                 520                 525
        Leu Arg Lys Lys Val Val Lys Arg Glu Asp Gly Arg Asn Phe Tyr Phe
                        530                 535                 540
        Tyr Glu Glu Gly Glu Arg Glu
        545                 550

<210> SEQ ID NO 3
```

```
-continued

<211> LENGTH: 23
<212> TYPE: DNA
<213> ORGANISM: Thermotoga neapolitana

<400> SEQUENCE: 3
agagcacctc gtatccacca gtc                                          23

<210> SEQ ID NO 4
<211> LENGTH: 23
<212> TYPE: DNA
<213> ORGANISM: Thermotoga neapolitana

<400> SEQUENCE: 4
ccacatacgc tccaccacca gat                                          23
```

THERMOSTABLE ALPHA-GALACTOSIDASE AND METHODS OF USE

This application claims priority to provisional application Ser. No. 60/057,047, filed Aug. 22, 1997, which is incorporated by reference herein.

FIELD OF THE INVENTION

This invention relates to microbial enzymes and their use in food processing. More specifically, this invention provides a novel thermostable α-galactosidase enzyme and its use in high-temperature processing of soy products to remove α-galactosides.

BACKGROUND OF THE INVENTION

Various scientific and scholarly articles are referred to throughout the specification. These articles are incorporated by reference herein to describe the state of the art to which this invention pertains.

The soybean (*Glycine max*) is a major American crop, both for oil and protein production. In 1990, the United States produced 45 billion pounds of soybean meal: 95% for animal feeds while 750 million pounds of soy protein ingredients were for human consumption. Soy is gaining popularity in the U.S., as research creates an awareness of the chemoprotective and cholesterol-reducing properties of certain soy components, and improves the taste for consumers (e.g., tofu cheddar cheese, soy milks. Production of edible protein ingredients continues to grow at about 15% per year (Greiner, 1990).

Soy use has been limited because of anti-nutritional compounds (e.g., trypsin inhibitors), allergens and flatus-causing oligosaccharides (Greiner, 1990). Soybeans typically contain 9–12% total sugars, including 4–5% sucrose, 1–2% raffinose, 3.5–4.5% stachyose, along melibiose and verbascose in smaller quantities (Greiner, 1990). Monogastric animals, including humans, lack the ability to synthesize sufficient α-galactosidase in their intestinal systems to hydrolyze the α-galactosides present in soybeans and other legumes. Thus α-galactosides (raffinose and stachyose) pass into the large intestine where the resident microbiota act on them, causing flatulence and gastrointestinal (GI) disturbance. These disturbances reduce both feed efficiency in monogastric animals and general consumer acceptance of soy foods. There is a high demand for α-galactoside-free soybean product.

Currently, the three methods of soy processing involve protein precipitation by acidification, ethanol extraction or heat coagulation, followed by alkali/high temperature resolubilization of the proteins (Wolf and Cowan, 1977). These methods are costly (estimated at $0.15–$0.20/lb of soybean meal) and often negatively affect the protein's functionality (Greiner, 1990). The oligosaccharides that are partially extracted in these processes are converted into soy molasses, and though partly used in the ruminant feed industry, their high BOD causes a major disposal problem.

Other methods of removing oligosaccharides in beans have been explored, including bean germination (Nanna and Phillips, 1988; Alani, et al., 1990); cooking (Anderson and Wolf, 1995; Reddy and Salunke, 1980); high temperature/high moisture extrusion (Borejszo and Khan, 1992) and the use of natural (Reddy and Salunke, 1980) or lactobacillus inoculants (*Lactobacillus fermentum*, *L. plantarum*, Duszkiewiz, et al., 1994). Motelongo et al., (1993) used the α-galactosidase-hydrolyzing activity of *L. salivarius* to convert soy molasses into lactic acid. α-galactosidases from Alpha-galactosidases (E.C.3.2.1.22) catalyze the hydrolysis of α-(1–6)-galactosyl linkages. These enzymes are found in microorganisms, plants and animals. The pH optimum for most α-galactosidases ranges from pH 4.0 to 7.5 and the temperature optimum is from 35 to 70° C. Relatively few reports address thermostable α-galactosidases: *B. stearothermophilus* optimum 70° C. (Ganter, et al., 1988; Tabot and Sygusch, 1990); Thermus strain T2 (Yoshinori et al., 1990); a novel thermophilic strain KM-THCJ (King et al., 1995) and *Thermotoga neapolitana* with an optimum at 100° C. (McCutchen, et al., 1996). However, genes encoding the thermostable α-galactosidases from these organisms heretofore have been unavailable.

The concept of incorporating into feed a yeast that expresses an α-galactosidase, in order to hydrolyze the flatulence oligosaccharides, has been considered from a recombinant DNA perspective. For example, fifteen copies (MIRK construct) of the gene from guar (*Cyamopsis tetragonoloba*) has been stably integrated and expressed in *Kluyveromyces lacits* (Hensing et al., 1995). However, the 15 gene copy MIRK construct only yielded 1.8 g protein/L). Moreover, the α-galactosidase produced by this organism is not thermostable.

Thermostable enzymes (also referred to as "thermozymes") are intrinsically stable and active a high temperature. Thermozymes from thermophiles and hyperthermophiles are optimally active at temperatures close to or above the optimal temperature for growth. The molecular mechanisms of thermal stability are not fully defined, although it is generally accepted that thermostability is a result of the accumulation of numerous changes. These include specific amino acid replacements; altered entropy of unfolding; tighter hydrophobic core packing helix stabilization; addition of disulfide bridges, salt bridges and hydrogen bonds. Given the complex factors involved in thermostabilization of proteins, an alternative strategy to engineering enzymes for enhanced thermal stability (for industrial applications) is to screen for thermostable enzymes from thermophiles. Furthermore such intrinsically thermostable enzymes can be altered to suit particular process requirements.

Thermotoga spp. fermentatively metabolize a variety of carbohydrates, including cellulose, xylan, starch and glycogen. To date, Thermotoga spp. are the only known hyperthermophiles capable of growing on cellulose. They produce a multiplicity of hydrolases with different specificities which are involved in the metabolism of various polysaccharide substrates. The list of enzymes characterized and cloned are extensive and include endoglucanases; cellobiohydrolase, β-glucosidases; β-galactosidases, endoxylanases, α-L-arabinofuranosidases and xylose isomerases. In addition McCutchen et al. (1996) recently described a β-mannanase and an α-galactosidase from *T. neapolitana* for hydrolysis of guar (galactomannan) gum. It would be an advance in the art to clone and characterize the gene or operon from *T. neapolitana* or any other species of Thermotoga that produces a thermostable α-galactosidase.

SUMMARY OF THE INVENTION

According to one aspect of the present invention, an isolated nucleic acid molecule from Thermotoga is provided, that includes an open reading frame encoding a thermostable α-galactosidase or subunit thereof. The α-galactosidase encoded by this nucleic acid molecule has an optimum temperature of activity of between about 84 and 100° C., preferably between about 89 and 97° C., and most preferably between about 92 and 94° C. It is stable for an extended period of time (i.e., at least four hours) at temperatures useful for industrial degradation of soybean galactosides (e.g., 65° C., preferably 70° C., most preferably 80° C. to 85° C.). It has a an optimum pH for activity between about 4.5 and 7.0, preferably pH 5 to pH 7, most preferably pH 5 to pH 6.

In a preferred embodiment, the isolated nucleic acid is from *Thermotoga neapolitana*. In another preferred embodiment, the open reading frame encodes an α-galactosidase having an amino acid sequence substantially the same as SEQ ID NO:2, and most preferably having SEQ ID NO:2. In a particularly preferred embodiment, the nucleic acid molecule comprises SEQ ID NO:1.

According to another aspect of the invention, an isolated nucleic acid molecule is provided, which has a sequence selected from the group consisting of: (a) SEQ ID NO:1; (b) a variant of Sequence I.D. No. 1: (c) a natural mutant of SEQ ID NO:1; (d) a sequence hybridizing with part or all of a sequence complementary to SEQ ID NO:1and encoding a polypeptide substantially the same as part or all of a polypeptide encoded by SEQ ID NO:1; and (e) a sequence encoding part or all of a polypeptide having amino acid SEQ ID NO:2.

According to another aspect of the invention, an isolated protein is provided, which is produced by expression of any of the aforementioned nucleic acid molecules.

According to another aspect of the invention, an isolated Thermotoga α-galactosidase, or subunit thereof, is provided. The α-galactosidase has an optimum temperature of activity of between about 84 and 100° C., preferably between about 89 and 97° C., and most preferably between about 92 and 94° C. It is stable for an extended period of time (i.e., at least four hours) at temperatures useful for industrial degradation of soybean galactosides (e.g., 65° C., preferably 70° C., most preferably 80° C. to 85° C.). It has a an optimum pH for activity between about 4.5 and 7.0, preferably pH 5 to pH 7, most preferably pH 5 to pH 6.

In a preferred embodiment, the enzyme is from *Thermotoga neapolitana*. In another preferred embodiment, the enzyme contains at least one polypeptide having an amino acid sequence substantially the same as SEQ ID NO:2.

According to another aspect of the invention, transgenic plants comprising a Thermotoga α-galactosidase gene are provided. These plants may be nuclear-transformed or plastid-transformed.

According to other aspects of the invention, methods are provided for using the thermostable α-galactosidase of the invention, and the gene encoding it, to deplete soy products of α-galactosides. Generally, the methods comprise heating the soy products to a temperature at least as high as about 65–70° C. (preferably 70–105° C., depending on the length of heating and other specifics of the material being heated), in the presence of an amount of the enzyme of the invention sufficient to cause depletion of the α-galactosides in a desired amount of time. Methods are also provided for depleting α-galactosides from other legumes or legume products requiring such treatment.

Other features and advantages of the present invention will become apparent upon consideration of the drawings, detailed description and examples set forth below.

BRIEF DESCRIPTION OF THE DRAWINGS

FIG. 1: Nucleotide sequence (SEQ ID NO:1) and aligned deduced amino acid sequence (SEQ ID NO:2) of a gene from *Thermotoga neapolitana* encoding a thermostable α-galactosidase.

FIGS. 3(A–D): Substrate, temperature and pH parameters of crude extracts of *Thermotoga neapolitana* α-galactosidase.

FIGS. 4(A–C): HPLC analysis of products of *Thermotoga neapolitana* enzymatic activity.

DETAILED DESCRIPTION OF THE INVENTION

I. Definitions

Figure 2:
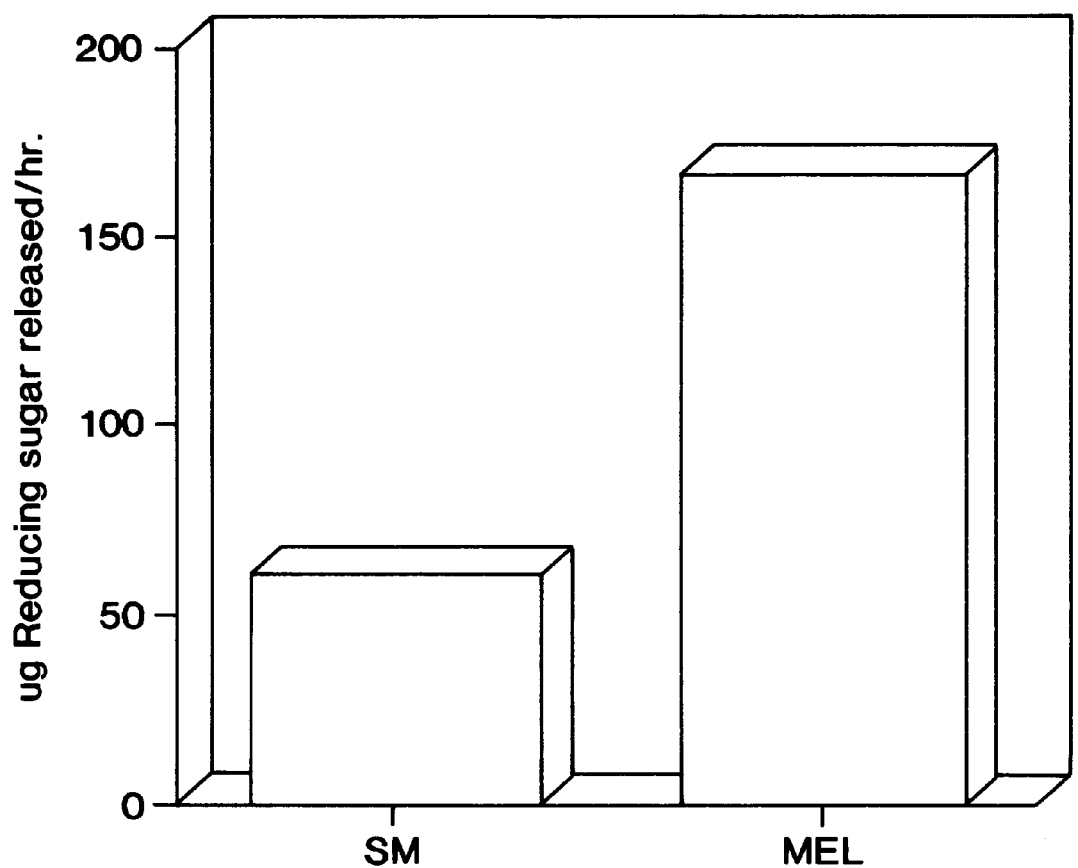
FIG. 2: Hydrolysis of soy molasses and melibiose by *Thermotoga neapolitana* (TA10α) recombinant α-galactosidase. (SM) soy molasses; (MEL) melibiose. Substrate reaction contains 3000 μg of α-1-6-containing galactosides.
Figure 3A:
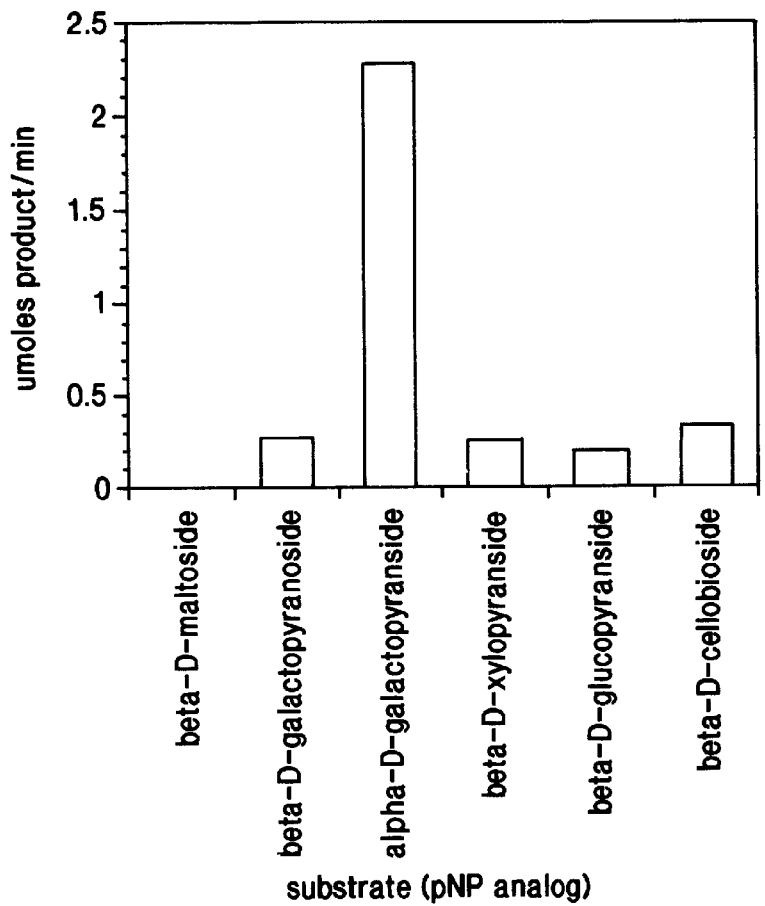
FIG. 3A shows the substrate specificity.
Figure 3B:
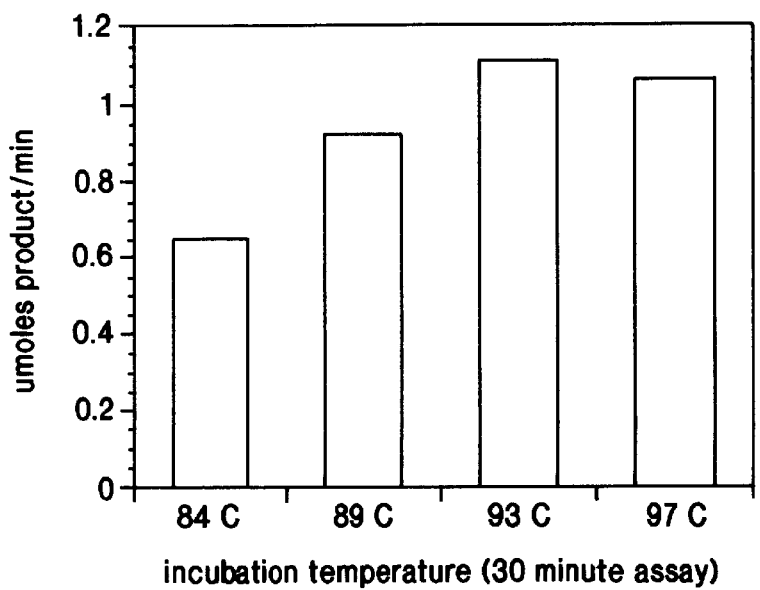
FIG. 3B shows the temperature optimum.
Figure 3C:
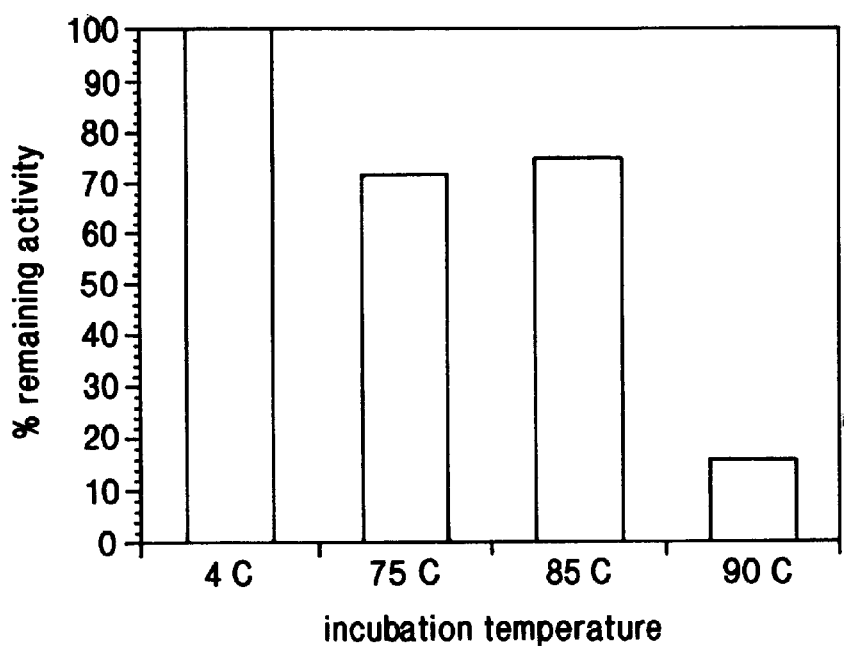
FIG. 3C shows the four-hour temperature stability.
Figure 3D:
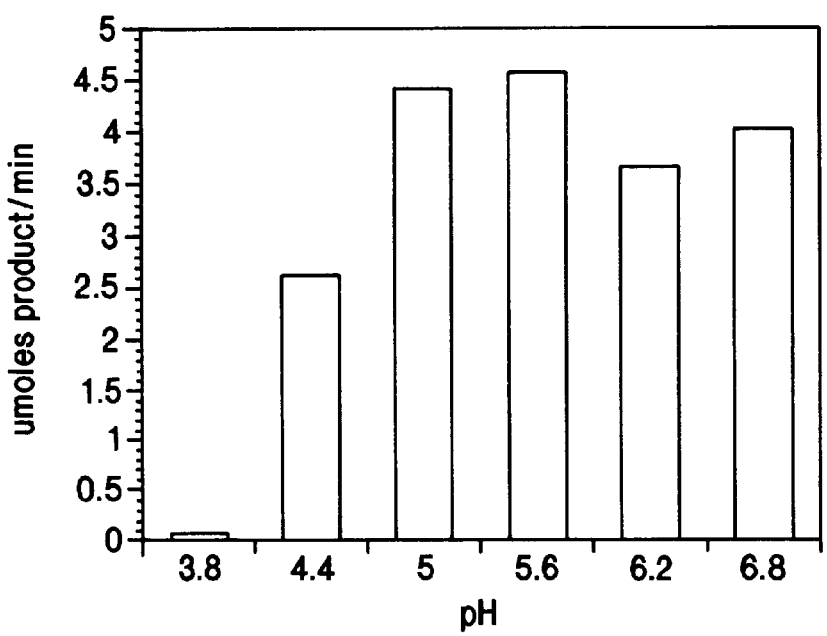
FIG. 3D shows the pH optimum.

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above.

Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, but not limited thereto, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the 5' regulatory regions of a gene, including promoters per se, but also including other 5' regulatory sequences such as translational regulators or enhancer elements.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants or other organisms (e.g., bacteria, yeast). When transforming plants, these constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Description

Provided in accordance with the present invention is a nucleic acid isolated from the thermophilic bacterium, Thermotoga, which encodes a thermostable α-galactosidase enzyme. A crude extract of the α-galactosidase produced by expression of the isolated gene possesses optimum activity between about 93 and 97° C., while retaining significant activity even after incubation at 84° C. for several hours.

Subcloning and sequencing of the Thermotoga gene provided DNA sequence and deduced amino acid sequence information showing strong similarity to that of other known raf-type α-galactosidases. The nucleotide sequence shows similarity to α-galactosidase-encoding genes from Pediococcus, Thermoanaerobacter, E. coli and Streptococcus. The gene was also found to reside in the T. neapolitana genome adjacent to a putative β-galactosidase gene, as has been the case for other α-gal genes of thermophilic bacteria (Yoshinori et al, 1990; Zverlov, 1996).

The 551 amino acid open reading frame of the gene translates to a protein of about 61 kDa, which correlates well to a 61 kDa protein that appears in crude extracts and partially purified extracts. Gel filtration analysis of the partially purified protein indicates a molecular mass of about 172 kDa, indicating that the enzyme may exist as a multimer.

The nucleotide sequence of the Thermotoga neapolitana α-galactosidase gene is set forth at the end of the specification (and in FIG. 1) as SEQ ID NO:1 (the sequence reads in the 5' to 3' direction). This gene is sometimes referred to herein as "tnαgal", to denote an α-galactosidase gene from Thermotoga neapolitana. The amino acid sequence deduced from SEQ ID NO: 1 is set forth at the end of the specification (and in FIG. 1) as SEQ ID NO:2.

It is believed that SEQ ID NO:1 constitutes a full-length α-galactosidase-encoding clone inasmuch as it expresses an active α-galactosidase in an E. coli expression system. The characteristics of the T. neapolitana α-galactosidase are described in greater detail in Examples 1 and 2. Although the α-galactosides from T. neapolitana is exemplified herein, This invention encompasses α-galactosidase genes and their encoded enzymes from any Thermotoga species, having the sequence, structural and functional properties of the α-galactosidase described herein. Thermostable α-galactosidase genes from Thermotoga species are sometimes referred to herein as Tαgal genes to denote that they are from Thermotoga, but not necessarily from Thermotoga neapolitana.

Variants and natural mutants of SEQ ID NO:1 are likely to exist within different species or strains of the Thermotoga genome. Because such variants are expected to possess certain differences in nucleotide and amino acid sequence, this invention provides an isolated nucleic acid molecule and an isolated thermostable α-galactosidase protein having at least about 50–60% (preferably 60–80%, most preferably over 80%) sequence homology in the coding region with the nucleotide sequence set forth as SEQ ID NO:1 (and, preferably, specifically comprising the coding region of SEQ ID NO: 1), and the amino acid sequence of SEQ ID NO:2. Because of the natural sequence variation likely to exist among these proteins and nucleic acids encoding them, one skilled in the art would expect to find up to about 40–50% sequence variation, while still maintaining the unique properties of the α-galactosidase of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin, and the parameters used by that program are the parameters intended to be used herein to compare sequence identity and similarity.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

III. Preparation of tαgal Nucleic Acid Molecules and Thermostable Thermotoga α-galactosidase A. Nucleic Acid Molecules Nucleic acid molecules encoding the α-galactosidase proteins of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length DNA having SEQ ID NO:1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.8 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.8 kb double-stranded molecule. A synthetic DNA molecule so constructed may then be cloned and amplified in an appropriate vector. Nucleic acid sequences encoding the α-galactosidase may be isolated from appropriate biological sources using methods known in the art. In a preferred embodiment, a genomic clone is isolated from a cosmid expression library of the *T. neapolitana* genome. In another embodiment, a genomic clone is isolated from a cosmid library of another Thermotoga genome.

In accordance with the present invention, nucleic acids having the appropriate level sequence homology with the protein coding region of SEQ ID NO:1 may be identified by using hybridization and washing conditions of appropriate stringency. For example, hybridizations may be performed, according to the method of Sambrook et al., using a hybridization solution comprising: 5× SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42–65° in 1× SSC and 1% SDS, changing the solution every 30 minutes.

One common formula for calculating the stringency conditions required to achieve hybridization between nucleic acid molecules of a specified sequence homology (Sambrook et al., 1989):

$$T_m=81.5° C.+16.6\text{Log}[Na+]+0.41(\% G+C)-0.63(\% \text{formamide})-600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

Tαgal nucleic acid molecules of the invention include DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the DNA having SEQ ID NO:1. Such oligonucleotides are useful as probes for detecting Tαgal genes or transcripts.

B. Proteins

A full-length α-galactosidase of the present invention may be prepared in a variety of ways, according to known methods. The protein may be purified from appropriate sources, e.g., cultured *T. neapolitana*.

The availability of nucleic acids molecules encoding the Thermotoga α-galactosidase enables production of the protein using in vitro expression methods known in the art. According to a preferred embodiment, the enzyme may be produced by expression in a suitable expression system. For example, part or all of a DNA molecule, such as the DNA having SEQ ID NO:1, may be inserted into a plasmid vector adapted for expression in a bacterial cell, such as *E. coli*, or a eucaryotic cell, such as *Saccharomyces cerevisiae* or other yeast. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The α-galactosidase produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners. In addition, the thermostability of the α-galactosidase can be used to facilitate its purification. A mixture of expression products can be heated to a temperature that degrades or denatures most proteins, but leaves the thermostable α-galactosidase intact. The intact protein is then separated from the degraded or denatured proteins.

The thermostable α-galactosidase of the invention, prepared by one of the aforementioned methods, may be analyzed according to standard procedures. For example, the protein may be subjected to amino acid sequence analysis, according to known methods. The stability and biological activity of the enzyme may be determined according to standard methods for assaying cleavage of the α-galactosidic bond. Examples of such methods are described in Examples 1 and 2 below.

The present invention also provides antibodies capable of immunospecifically binding to the α-galactosidase of the invention. Polyclonal antibodies may be prepared according to standard methods. In a preferred embodiment, monoclonal antibodies are prepared, which react immunospecifically with various epitopes of the protein. Monoclonal antibodies may be prepared according to general methods of Köhler and Milstein, following standard protocols. Polyclonal or monoclonal antibodies that immunospecifically interact with the α-galactosidase can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-α-galactosidase antibodies are described below.

IV. Uses of Thermotoga α-galactosidase Gene and Thermostable Thermotoga α-galactosidase A. Tαgal Nucleic Acids Tαgal nucleic acids may be used for a variety of purposes in accordance with the present invention. DNA, RNA, or fragments thereof may be used as probes to detect the presence of and/or expression tαgal genes. Methods in which tαgal nucleic acids may be utilized as probes for such assays include, but are not limited to: (1) in situ hybridization; (2) Southern hybridization (3) northern hybridization; and (4) assorted amplification reactions such as polymerase chain reactions (PCR).

The tαgal nucleic acids of the invention may also be utilized as probes to identify related genes from other Thermotoga species or from other thermophilic bacteria. As is well known in the art, hybridization stringencies may be adjusted to allow hybridization of nucleic acid probes with complementary sequences of varying degrees of homology.

As described above, tαgal nucleic acids are also used to advantage to produce large quantities of substantially pure thermostable α-galactosidase, or selected portions thereof. The enzyme is thereafter used for various commercial purposes, as described below.

In a preferred embodiment of the invention, large amounts of the recombinant Thermotoga α-galactosidase can be supplied in feed or in a soy processing reaction through the use of a transformed microorganism that expresses the tαgal gene. For instance, feed can be supplemented with a tαgal-expressing yeast, to produce a high quality soy product that is digestible by monogastric animals, such as chickens.

In another preferred embodiment of the invention, transgenic bean plants comprising the tαgal gene can be made, according to plant transformation methods known in the art. In one embodiment, nuclear transgenic plants are produced according to standard methods, e.g. by Agrobacterium-mediated transformation, electroporation or biolistic DNA delivery. In another embodiment, stably plastid-transformed plants comprising the gene are provided, e.g., by the methods set forth in U.S. Pat. No. 5,530,191 to Maliga et al. The tαgal gene can be expressed in transgenic plants, but will not be active until the plants (or plant parts) are heated to cooking temperature, e.g. 65° C. or above. Thus, when the soybeans (or any other legumes or plants producing α-galactosides) are processed, canned or otherwise heated, the thermostable α-galactosidase will become active and thereby destroy the α-galactosides in the beans, without the need for adding exogenous enzyme.

B. Thermotoga α-galactosidase

The Thermotoga α-galactosidase of the invention can be used for any purpose for which α-galactosidase is used. However, the thermostable enzyme offers major biotechnological advantages, including, but not limited to: higher reaction rates; lower viscosity and improved mass transfer; increased resistance to chemical denaturants; lower danger of contamination when operating at higher temperatures; higher product yields during certain chemical reactions due to chemical equilibrium shifts with higher temperature; and ease of purification by use of a heat treatment step.

Soybeans are processed by blanching or dry-heating, then grinding to produce a crude soybean meal. As one example of how the thermostable α-galactosidase can be used to advantage, this crude soy meal can be upgraded by heat treatment with the α-galactosidase to produce feeds that can be fed to non-ruminants, such as chicken and pigs. The heating step is necessary in any event to remove the anti-nutritional factor, trypsin inhibitor. The use of the α-galactosidase in this step further improves the digestibility and nutritional quality of the feed. In an alternative embodiment, the meal is moistened and processed by extrusion, which is intrinsically a heat-producing process. The heat of the extrusion process destroys the trypsin inhibitor and, in the presence of the thermostable α-galactosidase, likewise destroys the α-galactosides. The feed can be even further improved by supplementing the soy meal with a nutritional microorganism, such as yeast, containing the tαgal gene and producing the enzyme in situ when the meal is heated.

Crude soy meal is further process by solvent treatment to produce de-fatted soy flour. The thermostable α-galactosidase can also be used to advantage in any heated, cooked or baked product in which soy meal or defatted soy flour is presently used. Again, the enzyme is activated during the heating step and destroys any α-galactosides present in the meal or flour.

Soy milk and soy yogurt are produced by heating (blanching or dry heat), grinding, then extracting the beans with water. This process is well suited for improvement by treatment with a thermostable α-galactosidase. The enzyme is simply added to the extraction medium at the appropriate temperature, thereby eliminating the α-galactosides present in the aqueous extract (i.e., the soy milk).

The thermostable α-galactosidase of the invention can also be used to improve the dietary properties of other beans or legumes, many of which contain sufficient α-galactosides to cause flatulence and other gastrointestinal distress. Thus, any legume or legume product that is processed with a heating step (or to which a heating step can be added) can be treated with the enzyme of the invention during the heating process.

Another use for the thermostable α-galactosidase of the invention is in the processing of sugar from sugar beets. Raffinose, a trisaccharide, interferes with the crystallization of sucrose from sugar beet extract. The residual sugars after crystallization, i.e., the molasses, can be used as a substrate for alcohol fermentation. In molasses, the residual raffinose can be at 6% of solids, and is not fermentable by yeast. Treatment of sugar beet extract with the α-galactosidase of the invention results in hydrolysis of raffinose into its constituent sugars (galactose and sucrose), thereby improving the efficiency of crystallization of sucrose. In addition, hydrolytic products of raffinose are substrates for alcoholic fermentation by yeast, thus giving higher yield, greater efficiency of substrate utilization and less waste material.

The following examples are provided to describe the invention in further detail. These examples are intended to illustrate and not to limit the invention.

EXAMPLE 1

Cloning and Analysis of a *Thermotoga neapolitana* Gene Encoding a Thermostable α-galactosidase We describe in this example the isolation, cloning and expression of an -galactosidase from the ancient thermophilic eubacteria *Thermotoga neapolitana*.

MATERIALS AND METHODS

Bacterial strains, vectors and growth media. Bacterial strains and vectors are listed in Table 1 below:

| BACTERIAL STRAINS AND VECTORS | | |
|---|---|---|
| DESCRIPTION | CHARACTERISTICS/GENOTYPE | REF. SOURCES |
| BACTERIAL STRAINS *Escherichia coli* | | |
| DHα | F-,endA1,hsdR17, ($r_K^- m_K^-$), sup-E44, thi-1, recA1, gyrA96, relA1 | BRL,Inc. |
| XK1-Blue | recA1,endA1,gyrA96, thi-1, hsd-R17, supE4, relA1, lac[F' pro − A + B +, lacI qZΔM15, Tn10(tet')] | Stratagene |
| INVαF' | F'endA1,recA1,hsdR17($r_K^- m_K^+$) supE44,thi-1, gyrA96 relA1, φ80lacZΔM15, Δ(lacZYA-argF), U169 λ- | Invitrogen |

| BACTERIAL STRAINS AND VECTORS -continued | | |
|---|---|---|
| DESCRIPTION | CHARACTERISTICS/GENOTYPE | REF. SOURCES |
| Vectors | | |
| PLAFR3 | pLAFR1 containing HaeII fragment of pUC8 | Staskawicz et al., 1987 |
| pRU72 | PLAFR3 with a 24 kb insert α-galactos idase+ | This study |
| PTA10α | PCR2.1(Invitrogen) with 1.9 kb insert from PCR amplification of putative α-galactosidase gene (α-gal+) | This study |
| pP2α | pBluescript SK- with a PstI3.3 kb insert containing a partial α-galactosidase gene (αgal-) | This study |

*Thermotoga neapolitana* strain NS-E chromosomal DNA cosmid library (vector pLAFR3) contained within *E. coli* host strain DH was obtained from the laboratory of Dr. Kenneth Knoll, University of Connecticut, Storrs. *Escherichia coli* strains were grown in LB medium. Solid media contained 1.5% agar. Amipicillin (50 µg/ml), tetracycline (25 µg/ml), X-β-gal (20 µg/ml), and IPTG (40 µg/ml) were added when required.

DNA Techniques. DNA manipulation techniques, including plasmid isolations, restriction digests, ligations and transformation into *E. coli* and gel electrophoresis, were performed by standard methods.

Cosmid Screening. The *Thermotoga neapolitana* cosmid library was screened for -galactosidase activity. Individual cosmid colonies were grown overnight in 96 well microtiter plates in 100 µl of Superbroth containing 50 µg/ml tetracycline and incubated for 16 hrs at 37° C. with agitation. 100 µl of 4-methylumbelliferyl -galactopyranoside, dissolved in 50 mM phosphate-citrate buffer (pH 6.2), was added to a final concentration of 1 mM to each microtiter well. Toluene was added to a final concentration of 0.1% to permeablize cells. The microtiter plates were wrapped with plate seal (ISC Bioexpress) and incubated in a water bath at 80° C. After a 2 hr incubation, the microtiter plates were cooled and 0.5 M glycine-NaOH (pH 10.6) was added to each well followed by examination over a UV transilluminator. Potentially positive clones were grown overnight in 30 ml of LB (50 µg/ml tetracycline), and cells were harvested by centrifugation and resuspended in a volume of 1 ml with LB and frozen.

DNA Sequence Analysis. Plasmids isolated from subcloning protocols that contained at least 1 kb inserts were sequenced in the forward and reverse directions, using an automated sequencer (Applied Biosystems). Sequencing of the -galactosidase gene from the PCR amplified insert of RUC72 was performed by primer walking. Primers were designed from sequence of the pP2 sub-clone containing a portion of the -galactosidase gene.

PCR Amplification. To obtain the complete -galactosidase gene sequence, the 24 kb insert of RUC72 was amplified by the polymerase chain reaction. Amplification was conducted for 32 cycles using the following parameters: Denaturation at 94° C. for 3 min for one cycle, denaturation at 98° C. for 20 sec, annealing/extension at 68° C. for 20 min for 30 cycles, followed by a final and extension step at 72° C. for 10 min. PCR reactions contained 2.5 U of Takara Ex Taq DNA polymerase (Pan Vera Corp., Madison, Wis.), 1× LA Takara Buffer, 200 µM dNTPs, 50 ng of template and 0.2 μM of M13/pUC Forward (−47) and Reverse (−48) sequencing primers (New England Biolabs). PCR primers were removed using a Centricon-100 concentrator with a 100 kDa MW cut-off and product was used as template for sequencing reactions.

Based on the putative -galactosidase gene sequence, PCR primers were designed to amplify the expressing gene. Forward primer 5'-(AGAGCACCTCGTATCCAC CAGTC)-3' (SEQ ID NO:3) and reverse primer, 3'-(CCACATACGCTCCACCACCAGAT)-5' (SEQ ID NO:4) were synthesized. Amplification was conducted for 30 cycles using the following parameters: denaturation at 94° C. for 30 sec, annealing at 60° C. for 60 sec, and extension at 72° C. for 120 sec. PCR reactions contained 2.5 U of Takara Ex Taq DNA polymerase (Pan Vera Corp., Madison, Wis.), 1 Ex Taq Takara Buffer, 200 μM DNTPS, 50 ng of template and 0.2 μM of each primer. PCR primers were removed using a Qiaquick PCR product purification kit (Qiagen, California).

Expression of PCR Amplified Gene. The purified PCR product was ligated into pCR2.1 followed by transformation into INV F' One Shot Competent Cells (Invitrogen, California) and plated onto LA plates containing 50 μg/ml kanamycin and 40 μg/ml X-β-gal. Five-ml cultures grown from individual white colonies were screened for inserts by performing mini-preps and a duplicate culture was screened for activity using 10 mM (final concentration) p-nitrophenyl- -D-galactopyranoside (pNP G). The cell pellet from the harvested 5 ml culture was resuspended in 1 ml of 10 mM Bis-Tris Propane, pH 7.0. Cells were disrupted using a Mini-Bead-Beater apparatus (Biospec Products, Oklahoma). 10 μl of crude extract were added to 790 μl of 12.53 mM PNP G, 100 μl of ddH20 and 100 μl of pH 7.0 Bis-Tris Propane and assayed at 80° C. for 30 min. The reaction was terminated and color development performed by the addition of 2 ml of NaHCO₃. This method was used to characterize the optimum temperature and stability of crude -galactosidase. Restriction digests with EcoRI of -galactosidase containing sub-clones and negative control plasmids were performed to verify the presence of inserted DNA. The crude extract from RUC72 was tested for activity on other p-nitrophenyl glycosides. The following p-nitrophenyl glycosides were tested for hydrolysis using 10 mM of each dissolved in 25 mM Bis-Tris Propane: β-D-maltoside, β-D-galactopyranoside, -D-galactopyranoside, β-D-xyloside, β-D-glucopyranoside, and β-D-cellobioside.

N-Terminal amino acid sequence analysis. Recombinant -galactosidase from pTA10 was partially purified by ammonium sulfate fractionation and MonoQ ion exchange chromatography. 25 mM Bis-Tris Propane, pH 7.0 was used in both steps. Protein was eluted from the MonoQ column using a ascending gradient of 25 mM Bis-Tris Propane, 1 M NaCl buffer. The partially purified -galactosidase enzyme of PTA10 was electroblotted onto a PVDF membrane (Bio-Rad) and N-terminal sequence analysis was performed.

Electrophoresis. Enzyme purity was assessed by sodium dodecyl sulfate polyacrylamide gel electrophoresis (SDS-PAGE) using 10% gels as described by Laemmli (1970). Proteins were visualized by either coommassie blue or silver staining. Low MW standards were used for gel calibration (Pharmacia-LKB, Uppsala, Sweden).

Soy molasses hydrolysis. Soy oligosaccharide containing molasses was hydrolyzed at 80° C. 100 μl of 2% soy molasses dissolved in 10 mM Bis-Tris Propane (pH7.0) was added to 100 μl of enzyme solution and incubated at 80° C. for 1 hr. The amount of oligosaccharide hydrolyzed was determined using a reducing sugar assay [4]. Oligosaccharide concentration of both substrates is estimated to be ca. 3,000 μg.

RESULTS

Cloning of -galactosidase gene. Screening of the cosmid library yielded a cosmid-containing cell that expressed -galactosidase activity. Analysis of the crude extract demonstrated -galactosidase enzyme maintained approximately 75% and 10% activity after incubating at temperatures of 84 and 900° C. The crude enzyme demonstrated optimal activity of approximately 93° C. during 30 min incubation times using the PNP G assay. The enzyme demonstrated activity at higher temperatures however denaturation was seen after 15 min. of incubation. These results indicated that the enzyme was expressed from an -galactosidase gene of *Thermotoga neapolitana*, rather than being a false negative produced by the *E. coli* -galactosidase. The enzyme had little activity on other p-nitrophenyl substrates assayed, while possessing very high activity on the -1,6-galactopyranoside.

Sub-cloning of galactosidase gene. Cosmid DNA of RUC72 was digested with various restriction enzymes and ligated into pBluescript SK. Ligated plasmids were transformed into XL-1 Blue *E. coli* cells and screened for activity with p-nitrophyenyl- -D-galactopyranoside, which yielded no expressing -galactosidase. Random sequencing of plasmids containing larger inserts yielded sequence that had sequence similarity to other known -galactosidases. All of the sequences appear to be closely related to the raf-type -galactosidase of *E. coli* (Aslandis et al, 1989; Schmidt et al, 1976; Schmitt et al, 1979). The remainder of the insert was sequenced providing the majority of the -galactosidase gene. The missing 5' end of the gene was obtained by PCR amplifying the entire RUC72 cosmid insert, allowing primer walking for DNA sequencing to continue. The putative -galactosidase gene sequence is listed in FIG. 1. An ORF containing conserved deduced amino acid sequences similar to that of the other -galactosidases provides a gene with 1656 base pairs translating to a protein of 551 amino acids (and one stop codon) (ca. 61 kDa). Attempts to purify the enzyme to homogeneity have yielded the 61 kDa protein and a 61.5 kDa protein that are difficult to resolve for N-terminal sequencing. In heat treated gal+ and αgal− cultures, the 61 kDa enzyme does not occur in αgal− control cultures, but is present in αgal+ cultures. The enzyme is potentially N-terminally blocked as no N-terminal sequence could be obtained. The N-terminal sequence of the 61.5 kDa protein matches that of an *E. coli* malate synthetase.

PCR amplification, cloning and expression of the gene. The putative -galactosidase gene was PCR amplified and ligated into PCR2.1. Due to primer incompatibilities, the 5' primer was designed 40 bp upstream of the putative ribosome binding site and the 3' primer 200 bp from the putative stop codon. When the plasmid with the ligated insert was transformed into INVF ', an -galactosidase was expressed that showed activity at the 85° C. assay temperature. Numerous -galactosidase positive clones were obtained in this manner. These clones expressed a protein that was about 61 kDa in size. Partial purification yielded extracts with high -galactosidase activity containing the 61 kDa protein, although again it is very difficult to resolve the protein from a 61.5 kDa protein that is presumably expressed by *E. coli*. Sequencing of both the 5' and 3' end of PTA10 10 insert verified the presence of the desired gene.

Hydrolysis of Soy Molasses. Partially purified extracts containing the 61 kDa protein were used to hydrolyze soy molasses at 80° C. FIG. 3 demonstrates the activity of the recombinant enzyme on -1,6oligosaccharide containing soy molasses and melibiose. While the assay was not optimized with either substrate or optimized for enzyme concentration, obvious activity was observed on both substrates.

EXAMPLE 2

Purification and Characterization of *T. neapolitana* α-galactosidase Produced by Expression of *tn*αgal from Cosmid RUC 72 in an *E. coli* Expression System In this Example we describe the partial purification and enzymatic characteristics of a recombinant thermostable α-galactosidase produced by expression of the *T. neapolitana* α-galactosidase gene in *E. coli*.

MATERIALS AND METHODS

Sample preparation for activity assays. A 30 ml overnight Luria broth plus tetracycline (25 μg/ml) culture of *E. coli* containing cosmid RUC72 was centrifuged, resuspended to a total volume of 1 ml 25 mM BisTris buffer pH 6.2 and sonicated (5 cycles of 30 sec, on ice) to lyse the cells. After a 30 min heat treatment at 75° C. to denature *E. coli* proteins, the samples were microcentrifuged for 1 min at 15,000× g. The supernatant was used for activity screening. All assays were performed in triplicate.

Temperature optimum and stability assays. The optimum temperature for enzyme activity was measured by adding 5 μl of sample to 495 μl of 11.24 mM p-nitrophenyl-α-D-galactopyranoside (pNP-α-gal) in 25 mM BisTris pH 6.2 and incubating at 70° C. the enzyme reaction was terminated by adding 1 ml of NaHCO$_3$ and the colorimetric reaction was quanititated at 405 nm. Samples were assayed for activity at 0, 15 and 30 minutes. Temperature stability was assayed by incubating enzyme samples for four hours and then samples were taken from the temperature-treated aliquots and assayed by the procedure described above.

Substrate specificity assays. Five μl of sample was added to 495 μl of pNP analogs of various oligosaccharides in 25 mM Bis-Tris pH 6.2. Samples were incubated for 15 min at 80° C. The enzyme reaction was terminated by adding 1 ml of NaHCO$_3$ and the colorimetric reaction was quantitated at 405 nm.

Determination of optimum pH. Three-hundred fifty ml of citrate phosphate buffer, pH 3.8, 4.4, 5.0, 5.0, 6.2 or 6.8 (45 mM final) was combined with pNP-α-gal (4 mM final) and 50 ml of a 1:10 dilution crude enzyme. After a 10 min incubation at 90° C., 1.0 ml of 0.2 M glycine/NaOH buffer pH 10.5 was added to stop the reaction. Samples were diluted five-fold and the colorimetric reaction was quantitated at 405 nm.

Estimation of molecular weight by gel filtration. Crude extract was applied to a Superose-6 Gel filtration column to determine the MW of the active enzyme. It was estimated that the enzyme has a MW of 172 kDa. Enzyme fractions were assayed for α-D-galactosidase activity by adding 5 μl of sample to 495 μl of 10 mM pNP-α-gal in 25 mM BisTris pH 6.2 (Sigma Chemical Co., St. Louis, Mo.) and incubating for 30 min. at 80° C.

Partial purification of *T. neapolitana* α-galactosidase from *E. coli* cosmid clone. Protein concentration was measured by absorption at 280 nm. Enzyme activity units were based on mmoles/min of para-nitrophenol produced from pNP-α-gal in 75° C. Crude enzyme from 4L overnight Luria broth culture was prepared as previously described, then subjected to the following purification steps. Ammonium sulfate was added to the supernatant to bring it to 1M and loaded on a 20 mL Butyl Sepharose column equilibrated with 1 ammonium sulfate. The enzyme eluted at 0.0 M ammonium sulfate and was then loaded on a MonoQ (anion exchange) column. The enzyme eluted off the MonoQ column at approximately 300 mM NaCl.

One unit of the MonoQ eluent was electrophoresed in a native gradient gel (4–15%) and stained with methylumbelliferyl-α-galactose to reveal the active band. The gel was then Coomassie stained to reveal all protein bands. A purity of 10% was approximated from the resulting bands on the gel.

HPLC analysis of α-galactosidase digestion of oligosaccharides. Ninety μl of stachyose or raffinose (20 mM final) were incubated with and without the addition of 10 μl of partially purified α-galactosidase for 40 min at 80° C. in 20 mM BisTris pH 6.0. Samples and standards were then analyzed by isocratic size-exclusion HPLC on a BioRad AMINEX HPX-87C column and products detected by refractive index. The column temperature was 85° C.; flow rate was 0.2 ml/min with water as the mobile phase.

RESULTS

Figure 4A:
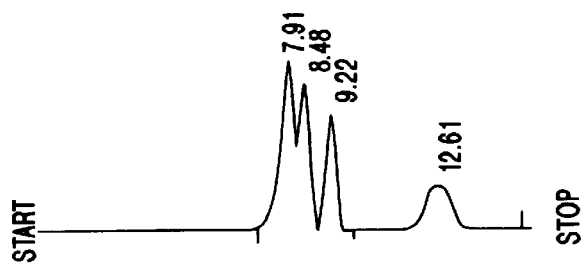
FIG. 4A shows HPLC analysis of undigested products.
Figure 4B:
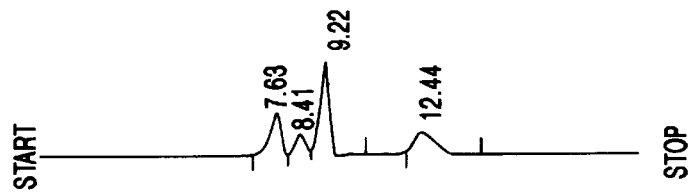
FIG. 4B shows HPLC analysis of raffinose digested with the enzyme.
Figure 4C:
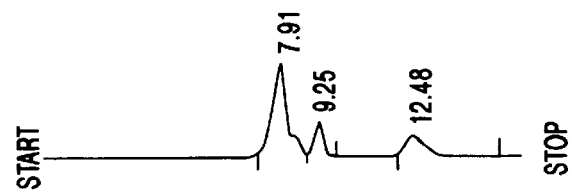
FIG. 4C shows HPLC analysis of stachyose digested with the enzyme. Retention times on the HPLC column are indicated at the bottom of the figure.

Clearly, the *T. neapolitana* α-galactosidase meets the process requirements for removal of flatulence oligosaccharides during the heat treatment step used to inactivate soy trypsin inhibitor. Showing high specificity for cleavage of α-galactoside bonds (FIG. 3, Graph 1,) the partially purified enzyme displayed a temperature optimum of 93° C. under the assay conditions described above (FIG. 3, Graph 2) and a broad pH range, retaining greater than 80% activity between pH 5 to 6.8 (FIG. 3, Graph 3). After four hours at 85° C., more than 75% activity remains, indicating high thermostability (FIG. 3, Graph 4). Moreover, significant digestion of raffinose and stachyose, the primary flatulence oligosaccharides in soy meal, occurs at conditions similar to those used in the soy heat treatment step. A forty minute digestion of these sugars at 80° C. resulted in the removal of 86% of raffinose (FIG. 4B) and significant degradation of stachyose into raffinose, sucrose and galactose (FIG. 4C).

Table 2 below shows the steps and purification achieved in a partial purification of *T. neapolitana* α-galactosidase expressed in *E. coli* from cosmid clone RUC72.

TABLE 2

| Sample | Protein (mg) | Units | Units/mg | Yield (%) | Purity (%) |
|---|---|---|---|---|---|
| Initial Material | 3852 | 160 | 0.04 | 100 | 0.003 |
| Heat Treatment | 324 | 165 | 0.51 | 103 | 0.03 |
| Butyl Sepharose | 3.6 | 72 | 20.00 | 45 | 1.3 |
| Mono Q | 0.34 | 52 | 152.94 | 33 | 10 |

Partial purification of the recombinant enzyme has been achieved and shows specific activity of 152.3 U/mg. The enzyme has a molecular mass of 172 kDa as determined by gel filtration (data not shown) suggesting that the enzyme may exist as a multimer of the 61 kDa polypeptide described in Example 1.

REFERENCES

Aduse-Opoku, J., L. Tao, J. Ferretti, and R. Russell. 1991. Biochemical and genetic analysis of *Streptococcus mutans* -galactosidase. J. Gen Microbiol. 137:757–764.

Annunziato, M., R. Manoney, and R. Mudgett. 1986. Production of -galactosidase from *Aspergillus oryzae* grown in solid state culture. J. Food Science. 51: 1370–1371.

Aslandis, C., K. Schmidt, and R. Schmitt. 1989. Nucleotide sequences and operon structure of plasmid-borne genes mediating uptake and utilization of raffinose in *Escherichia coli*, J Bact. 171:6753–6753.

Bernfeld, P. 1955. Amylases. and α Methods Enzymol. 1:149–158.

Calloway, D., C. Hickey, and E. Murphy. 1971. Reduction of intestinal gas-forming properties of legumes by traditional and experimental food processing methods. J Food Sci 36:251–255.

Cruz, R., J. Batistela, and G. Wosiacki. 1981. Microbial -galactosidase for soy milk processing, J Food Sci. 47:1973.

Delente, J., J. Johnson, M. Kuo, R. Conner, and L. Weeks. 1974. Production of a new thermostable neutral -galactosidase from a strain of *Bacillus stearothermophilus*. Biotech. Bioeng. 16:1227–1243.

Devereux, J., P. Haeberli, and O. Smithies. 1984. A comprehensive set of sequence analysis programs for the VAX. Nucleic Acids Research. 12:387–395.

Duffaud, G., C. McCutchen, P. Leduc, K. Parker, and R. Kelly. 1997. Purification and characterization of extremely thermostable β-mannanase, β-mannosidase, and -galactosidase from the hyperthermophilic eubacterium *Thermotoga neapolitana* 5068. Appl Env Micro. 63:169–177.

Garro, M., G. Devaldez, G. Oliver, and G. Degiori. 1996. Purification of -galactosidase from *Lactobacillus fermentum*, J Biotechnol. 45:103–109.

Greiner, C., ed. Economic implication of modified soybean traits. Iowa Soybean Promotion Board, 1990, Iowa State University: Iowa Agriculture and Home Economics Experiment Station.

Laemmli, U. 1970. Cleavage of structural proteins during the assembly of the head of bacteriophage T4. Nature (London). 227: 680–685.

McCutchen, C., G. Duffaud, P. Leduc, A. Peterson, A. Tayal, S. Khan, and R. Kelly. 1996. Characterization of extremely thermostable enzymatic breakers ( -1,6-galactosidase and β-1,4-mannanase) from the hyperthermophilic bacterium *Thermotoga neapolitana* 5068 for hydrolysis of guargum. Biotechnol Bioeng. 52:332–339.

Reynolds, J. 1974. An immobilized -galactosidase continuous flow reactor. Biotechnol Bioeng. 16: 135–147.

Schmidt, K. and R. Schmitt. 1976. Raffinose metabolism in *Escherichia coli* K12. Purification and properties of a new -galactosidase specified by a transmissible plasmid. Eur J Biochem. 67–:95–104.

Schmitt, R., R. Mattes, K. Schmidt, and J. Altenbucher. 1979. Raf plasmids in strains of *E. coli* and their possible role in enteropathogeny, pp. 199–210. K. Timmis and A. Puhler. (Eds), Plasmids of medical, environmental and commercial importance, Elsevier/North Holland Publishing Co., Amsterdam.

Staskawicz, B., D. Dahlbeck, N. Keen, and C. Napoli, 1987. Molecular characterization of cloned avirulence genes from Race 0 and Race 1 of *Pseudomonas syringae* pv. glycinea. J. Bacteriol. 169: 5789–5794.

Yoshinori, K., S. Okamoto, and K. Furukawa. 1990. Cloning of - and β-Galactosidase genes from an extreme thermophile, Thermus Strain T2, and their expression in *Thermus thermophilus* HB27. Appl Env Microbiol 56: 2251–2254.

Zverlov, V. 1996. *Thermoanaerobacter ethanolicus* melA and lacA genes. Unpublished genebank submission Y08557.

The present invention is not intended to be limited to the preferred embodiments described and specifically exemplified above. Various modifications may be made thereto without departing from the scope and spirit of the present invention, as set forth in the following claims.

What is claimed is:

1. An isolated nucleic acid molecule from *Thermotoga neapolitana* that comprises an open reading frame encoding a thermostable α-galactosidase and possess the same enzymatic activity as the protein having the amino acid sequence of SEQ ID NO:2.

2. The nucleic acid molecule of claim 1, wherein the open reading frame encodes an α-galactosidase having an optimum temperature range for activity of between 80° C. and 100° C.

3. The nucleic acid molecule of claim 2, wherein the open reading frame encodes SEQ ID NO:2.

4. The nucleic acid molecule of claim 3, which comprises SEQ ID NO:1.

5. A recombinant DNA molecule comprising the nucleic acid molecule of claim 1, operably linked to a vector.

6. A cell transformed with the recombinant DNA molecule of claim 5, selected from the group consisting of bacterial cells and plant cells.

7. A transgenic plant regenerated from the transformed cell of claim 6.

8. An isolated nucleic acid molecule having a sequence selected from the group consisting of:
   a) SEQ ID NO:1;
   b) sequence hybridizing with SEQ ID NO:1 or its complement under hybridization conditions calculated to achieve hybridization between two single-stranded DNA molecules of greater than 80% homology, using a formula of:

$T_m$=81.5° C.+16.6Log[Na+]+0.41 (% G+C)−0.63(% formamide)−600/#bp in duplex, wherein the $T_m$ of a DNA duplex decreases by 1–1.5° C. with every 1% decrease in homology; and c) a sequence encoding a polypeptide having amino acid SEQ ID NO:2;

wherein said isolated nucleic acid molecule has encodes a protein having the amino acid sequence of SEQ ID NO:2.

9. A recombinant DNA molecule comprising the nucleic acid molecule of claim 8, operably linked to a vector.

10. A cell transformed with the recombinant DNA molecule of claim 9, selected from the group consisting of bacterial cells and plant cells.

11. A transgenic plant regenerated from the cell of claim 10.

12. A method of depleting soybeans of α-galactosides, which comprises providing transgenic, fertile soybean plants that produce an enzymatically active *Thermotoga neapolitana* α-galactosidase possessing the same enzymatic activity as the protein having the amino acid sequence of SEQ ID NO:2, growing the plants, harvesting soybeans from the plants, and heating the soybeans for a time and at a temperature effective to deplete the α-galactosides from the soybeans.

* * * * *